(12) United States Patent
Shyur et al.

(10) Patent No.: US 7,527,958 B2
(45) Date of Patent: May 5, 2009

(54) TRUNCATED 1,3-1,4-β-D-GLUCANASE

(75) Inventors: Lie-Fen Shyur, Taipei (TW); Tuan-Nan Wen, Taipei (TW); Shu-Hua Lee, Taipei (TW); Ning-Sun Yang, Taipei (TW)

(73) Assignee: Academia Sinica, Taipei (TW)

( * ) Notice: Subject to any disclaimer, the term of this patent is extended or adjusted under 35 U.S.C. 154(b) by 804 days.

(21) Appl. No.: 10/773,455

(22) Filed: Feb. 6, 2004

(65) Prior Publication Data

US 2005/0009164 A1 Jan. 13, 2005

Related U.S. Application Data

(63) Continuation-in-part of application No. 09/654,652, filed on Sep. 5, 2000, now Pat. No. 7,037,696.

(51) Int. Cl.
| | |
|---|---|
| C12N 9/26 | (2006.01) |
| C12N 1/20 | (2006.01) |
| C12N 15/00 | (2006.01) |
| C12Q 1/68 | (2006.01) |
| C12Q 1/34 | (2006.01) |
| C12Q 21/04 | (2006.01) |
| C07H 21/04 | (2006.01) |
| C12Q 1/00 | (2006.01) |

(52) U.S. Cl. ............... 435/201; 435/4; 435/6; 435/18; 435/69.1; 435/71.1; 435/252.3; 435/320.1; 435/440; 536/23.2

(58) Field of Classification Search ........................ None
See application file for complete search history.

(56) References Cited

U.S. PATENT DOCUMENTS 7,037,696 B1 * 5/2006 Shyur et al. .................. 435/189

OTHER PUBLICATIONS

Branden et al. Introduction to Protein Structure, Garland Publishing Inc., New York, p. 247, 1991.*
Keitel et al. "Molecular and active-site structure of a *bacsillus* 1,3-1,4-beta-glucanase". Proc. Natl. Acad. Sci. USA 90:5287-5291, 1993.
Schimming et al. "Structure of the *Clostridium thermocellum* gene *lic B* and the encoded beta-1,3-1,4-glucanase". Eur. J. Biochem. 204:13-19, 1992.
Teather et al. "DNA sequences of a *Fibrobacter succinogenes* mixed-linkage beta-glucanase (1,3-1,4-beta-D-flucanohydrolase) gene". Journal of Bacteriology 172(7):3837-3841, Jul. 1990.
Henrissat. "A classification of glycosyl hydrolases based on amino acid sequence similarities". Biochem J. 280:309-316, 1991.
Henrissat et al. "New families in the classification of glycosyl hydrolases based on amino acid sequence similarities". Biochem J. 293:781-788, 1993.
Chen et al. "Sequencing of a 1,3-1,4-beta-D-glucanase (lichenase) from the anaerobic fungus *Orpinomyces* strain PC-2: Properties of the enzyme expressed in *Escherichia coli* and evidence that the gene has a bacterial origin". Journal of Bacteriology 179(19):6028-6034, 1997.
Erfle et al. "Purification and properties of a 1,3-1,4-beta-D-glucanase (lichenase, 1,3-1,4-beta-D-glucan 4-glucanolhydrolase, EC 3.2.1.73) from *Bacteriodes succinogenes* cloned in *Escherichia coli*". Biochem J. 255:833-841, 1988.
Sanger et al. "DNA sequencing with chain-terminating inhibitors". Proc. Natl. Acad. Sci. USA 74(12):5463-5467, 1977.
Laemmli. "Cleavage of structural proteins during the assembly of the head of bacteriophage T4". Nature 227:680-685, 1970.
Bradford. "A rapid and sensitive method for the quantitation of microgram quantities of protein utilizing the principle of protein-dye binding". Analytical Biochemistry 72:248-254, 1976.
Cai et al. "Structural studies on folding intermediates of serine hydroxymethyltransferase using single tryptophan mutants". Journal of Biological Chemistry 271(6):2987-2994, 1996.
Heinemann et al. "Circular permutations of protein sequence: not so rare?" Letters TIBS 20: 349-350, 1995.
Bedford et al. "The effect of dietary enzyme supplementation of rye- and barley-based diets on digestion and subsequent performance in weanling pigs". Can. J. Anim. Sci 72:97-105, 1992.
Selinger et al. "The Rumen: A unique source of enzymes for enhancing livestock production". Anaerobe 2:263-284, 1996.
Wettstein et al. "Improved barley broiler fees with transgenic malt containing heat-stable (1,3-1,4)-beta-glucanase". PNAS 97(25):13512-13517, 2000.
Miller. "Use of dinitrosalicylic acid reagent for determination of reducing sugar". Analytical Chemistry 31(3):426-428, 1959.
Chen et al. "Directed mutagenesis of specific active site residues on *Fibrobacter succinogenes* 1,3-1,4-beta-D-glucanase significantly affects catalysis and enzyme structural stability". Journal of Biological Chemistry 276(21):17895-17901, 2001.
Cheng et al. "Mutagenesis of $Trp^{54}$ and $Trp^{203}$ residues on *Fibrobacter succinogenes* 1,3-1,4-beta-D-glucanase significantly affects catalytic activities of the enzyme". Biochemistry 41:8759-8766, 2002.
Heinemann et al. "Enzymology and folding of natural and engineered bacterial beta-glucanases studied by x-ray christallography". Biol. Chem. 377:447-454, 1996.

* cited by examiner

*Primary Examiner*—Yong D Pak
(74) *Attorney, Agent, or Firm*—Occhiuti Rohlicek & Tsao LLP

(57) ABSTRACT

A truncated 1,3-1,4-β-D-glucanase. Also disclosed are related nucleic acid, vector, host cell, and preparation method.

13 Claims, No Drawings

TRUNCATED 1,3-1,4-β-D-GLUCANASE

RELATED APPLICATION

This application is a continuation-in-part of U.S. application Ser. No. 09/654,652, filed Sep. 5, 2000, now issued as U.S. Pat. No. 7,037,696, which is incorporated by reference in its entirety.

BACKGROUND 1,3-1,4-β-D-glucanase, an enzyme often found in ruminal bacteria, cleaves a β-1,4-glucosidic linkage adjacent to β-1,3-linkages in mixed linkage β-glucans, such as lichenan or barley β-glucan, producing cellobiosyltriose and cellotriosyltetraose. It facilitates plant fiber degradation in the rumens of ruminal animals and therefore has been used as a supplement for non-ruminal animals to increase feed conversion efficiency and animal growth-rate. This enzyme has also been used to substitute for or supplement malt enzymes in beer brewing to reduce processing problems caused by β-glucans from cell walls of the starchy seed endosperm, such as reduced rates of wort separation and beer filtration, and formation of hazes and gelatinous precipitates in beer. Nonetheless, the use of this enzyme has been limited by its low catalytic activity and thermal instability. Thus, there is a need for 1,3-1,4-β-D-glucanase that is both highly active and heat resistant.

SUMMARY

This invention is based, at least in part, on the unexpected discovery that truncated forms of *Fibrobacter succinogenes* 1,3-1,4-β-D-glucanase ("truncated glucanases") exhibit higher enzymatic activity and heat-resistance than the wild type 1,3-1,4-β-D-glucanase.

The amino acid sequence of the wild type *Fibrobacter succinogenes* 1,3-1,4-β-D-glucanase (SEQ ID NO: 1) and the nucleotide sequence (SEQ ID NO: 6) encoding it are listed below:

```
ATGAACATCAAGAAAACTGCAGTCAAGAGCGCTCTCGCCGTAGCAGCCGCAGCAGCAGCC
 M   N   I   K   K   T   A   V   K   S   A   L   A   V   A   A   A   A   A   A      20

CTCACCACCAATGTTAGCGCAAAGGATTTTAGCGGTGCCGAACTCTACACGTTAGAAGAA
 L   T   T   N   V   S   A   K   D   F   S   G   A   E   L   Y   T   L   E   E      40

GTTCAGTACGGTAAGTTTGAAGCCCGTATGAAGATGGCAGCCGCATCGGGAACAGTCAGT
 V   Q   Y   G   K   F   E   A   R   M   K   M   A   A   A   S   G   T   V   S      60

TCCATGTTCCTCTACCAGAATGGTTCCGAAATCGCCGATGGAAGGCCCTGGGTAGAAGTG
 S   M   F   L   Y   Q   N   G   S   E   I   A   D   G   R   P   W   V   E   V      80

GATATTGAAGTTCTCGGCAAGAATCCGGGCAGTTTCCAGTCCAACATCATTACCGGTAAG
 D   I   E   V   L   G   K   N   P   G   S   F   Q   S   N   I   I   T   G   K     100

GCCGGCGCACAAAAGACTAGCGAAAAGCACCATGCTGTTAGCCCCGCCGCCGATCAGGCT
 A   G   A   Q   K   T   S   E   K   H   H   A   V   S   P   A   A   D   Q   A     120

TTCCACACCTACGGTCTCGAATGGACTCCGAATTACGTCCGCTGGACTGTTGACGGTCAG
 F   H   T   Y   G   L   E   W   T   P   N   Y   V   R   W   T   V   D   G   Q     140

GAAGTCCGCAAGACGGAAGGTGGCCAGGTTTCCAACTTGACAGGTACACAGGGACTCCGT
 E   V   R   K   T   E   G   G   Q   V   S   N   L   T   G   T   Q   G   L   R     160

TTTAACCTTTGGTCGTCTGAGAGTGCGGCTTGGGTTGGCCAGTTCGATGAATCAAAGCTT
 F   N   L   W   S   S   E   S   A   A   W   V   G   Q   F   D   E   S   K   L     180

CCGCTTTTCCAGTTCATCAACTGGGTCAAGGTTTATAAGTATACGCCGGGCCAGGGCGAA
 P   L   F   Q   F   I   N   W   V   K   V   Y   K   Y   T   P   G   Q   G   E     200

GGCGGCAGCGACTTTACGCTTGACTGGACCGACAATTTTGACACGTTTGATGGCTCCCGC
 G   G   S   D   F   T   L   D   W   T   D   N   F   D   T   F   D   G   S   R     220

TGGGGCAAGGGTGACTGGACATTTGACGGTAACCGTGTCGACCTCACCGACAAGAACATC
 W   G   K   G   D   W   T   F   D   G   N   R   V   D   L   T   D   K   N   I     240

TACTCCAGAGATGGCATGTTGATCCTCGCCCTCACCCGCAAAGGTCAGGAAAGCTTCAAC
 Y   S   R   D   G   M   L   I   L   A   L   T   R   K   G   Q   E   S   F   N     260

GGCCAGGTTCCGAGAGATGACGAACCTGCTCCGCAATCTTCTAGCAGCGCTCCGGCATCT
 G   Q   V   P   R   D   D   E   P   A   P   Q   S   S   S   S   A   P   A   S     280

TCTAGCAGTGTTCCGGCAAGCTCCTCTAGCGTCCCTGCCTCCTCGAGCAGCGCATTTGTT
 S   S   S   V   P   A   S   S   S   V   P   A   S   S   S   S   A   F   V     300

CCGCCGAGCTCCTCGAGCGCCACAAACGCAATCCACGGAATGCGCACAACTCCGGCAGTT
 P   P   S   S   S   S   A   T   N   A   I   H   G   M   R   T   T   P   A   V     320

GCAAAGGAACACCGCAATCTCGTGAACGCCAAGGGTGCCAAGGTGAACCCGAATGGCCAC
 A   K   E   H   R   N   L   V   N   A   K   G   A   K   V   N   P   N   G   H     340

AAGCGTTATCGCGTGAACTTTGAACACTAA
 K   R   Y   R   V   N   F   E   H   *                                           349
```

The enzyme contains (1) a 27 amino acid (aa) signal sequence (SEQ ID NO: 2) at its N terminus; (2) two catalytic domains, i.e., domains A (aa 28-202, SEQ ID NO: 3) and B (aa 203-266, SEQ ID NO: 4); and (3) a C-terminal part. A truncation of the 78 residues from the C terminus (aa 272-349, SEQ ID NO: 5, underlined) generates a highly active and heat-resistant glucanase.

Accordingly, one aspect of this invention features an isolated polypeptide that contains the enzymatic catalytic domains of 1,3-1,4-β-D-glucanase and excludes the carboxyl terminal 78 amino acid residues of this enzyme. An "isolated polypeptide" refers to a polypeptide that has been separated from other proteins, lipids, and nucleic acids with which it is naturally associated. It can be a preparation that contains at least 10% (i.e., any number between 10% and 100%, inclusive) by dry weight the pure polypeptide. The enzymatic catalytic domains include SEQ ID NOs: 3 and 4, or their functional equivalents. A functional equivalent refers to a polypeptide derived from an enzymatic catalytic domain of 1,3-1,4-β-D-glucanase, e.g., a fusion protein or a protein having one or more point mutations, insertions, deletions, truncations, or a combination thereof. It retains substantially the activity of 1,3-1,4-β-D-glucanase, i.e., the ability to cleave β-1,4-glucosidic bonds. In one embodiment, the isolated polypeptide contains the aa V25-P271 of SEQ ID NO: 1 (SEQ ID NO: 7). This sequence can be linked to a tag sequence at its N or C terminus. For example, its C terminus can be fused to a tag NSSVDKLAA (SEQ ID NO: 12) or NSSVDKLAAALEHHHHHH (SEQ ID NO: 16) to form a fusion protein SEQ ID NO: 9 or 14. Since these two tags bind to commercially available antibodies and $Ni^{2+}$ NTA resin, respectively, fusing either of them facilitates the purification of the fusion protein. In another embodiment, an isolated polypeptide of this invention contains a sequence identical to SEQ ID NO: 7 except that the tryptophan (W) at position 203 is replaced by a phenylalanine (F). This mutant sequence (SEQ ID NO: 8) can also be linked to one of the two just-described tags at its C or N terminus, e.g., at its C terminus to form a fusion protein SEQ ID NO: 13 or 15. Preferably, the above-described polypeptide is glycosylated.

This invention also features an isolated nucleic acid having a sequence that encodes the above-described polypeptide. An "isolated nucleic acid" refers to a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The nucleic acid of this invention can be used to express the polypeptide of this invention. For this purpose, one can operatively link the nucleic acid to suitable regulatory sequences to generate an expression vector.

A vector refers to a nucleic acid molecule capable of transporting another nucleic acid to which it has been linked, and also capable of autonomous replication or integration into a host DNA. Examples include a plasmid, cosmid, and viral vector. A vector of this invention includes a nucleic acid in a form suitable for expression of the nucleic acid in a host cell. Preferably, the vector includes one or more regulatory sequences operatively linked to the nucleic acid sequence to be expressed. Examples of a "regulatory sequence" include promoters, enhancers, and other expression control elements (e.g., polyadenylation signals). Regulatory sequences also include those that direct constitutive expression of a nucleotide sequence, as well as tissue-specific regulatory and/or inducible sequences. The design of such an expression vector is based on considerations including the choice of the host cell to be transformed and the desired expression level. An expression vector can be introduced into host cells to produce the polypeptide of this invention. Also within the scope of this invention is a host cell that contains the above-described nucleic acid. The host cell can be a bacterial cell, a yeast cell, an insect cell, a plant cell, and a mammalian cell. Preferably, it is an *E. coli* or *P. pastoris* cell.

To produce a polypeptide of this invention, one can place a host cell in a culture under conditions permitting expression of a polypeptide encoded by a nucleic acid described above, and isolate the polypeptide from the culture. Alternatively, the nucleic acid of this invention can be transcribed and translated in vitro, for example, using T7 promoter regulatory sequences and T7 polymerase.

The details of one or more embodiments of the invention are set forth in the accompanying description below. Other advantages, features, and objects of the invention will be apparent from the detailed description and the claims.

DETAILED DESCRIPTION

This invention relates to truncated glucanases and their variants. The variants include biologically active fragments whose sequences differ from the truncated glucanase sequences described herein by one or more conservative amino acid substitutions or by one or more non-conservative amino acid substitutions, deletions, or insertions that do not abolish the catalytic activity.

A truncated glucanase of this invention or its variant can be produced by using an expression vector that contains an isolated nucleic acid of this invention. The vector can be designed for expression of a truncated glucanase in prokaryotic or eukaryotic cells, such as bacterial cells (e.g., *E. coli*), yeast cells (e.g., *P. pastoris*), insect cells, plant cells, and mammalian cells. Suitable host cells are discussed in Goeddel, (1990) *Gene Expression Technology: Methods in Enzymology* 185, Academic Press, San Diego, Calif. Expression of a truncated glucanase can be carried out with vectors containing constitutive or inducible promoters directing the expression of either a fusion or a non-fusion truncated glucanase. Fusing a tag to the amino or carboxyl terminus of a truncated glucanase facilitates purification of soluble glucanase. Examples of a tag include multiple histidines, glutathione S-transferase (GST), maltose E binding protein, protein A, and suitable peptide epitopes, e.g., HA, Myc, and FLAG.

A vector can be introduced into host cells via conventional transformation or transfection techniques, such as calcium phosphate or calcium chloride co-precipitation, DEAE-dextran-mediated transfection, lipofection, or electroporation. After being transformed or transfected with a vector of this invention, a host cell can be cultured in a medium to express a truncated glucanase. The expressed truncated glucanase can then be isolated from the host cell or from the culture medium using standard techniques.

If an expressed truncated glucanase is fused to one of the tags described above, the truncated glucanase can be easily purified from a clarified cell lysate or culture medium with an appropriate affinity column, e.g., $Ni^{2+}$ NTA resin for hexahistidine, glutathione agarose for GST, amylose resin for maltose binding protein, chitin resin for chitin binding domain, and antibody affinity columns for epitope tagged proteins. The truncated glucanase can be eluted from the affinity column, or if appropriate, cleaved from the column with a site-specific protease. If the truncated glucanase is not tagged for purification, routine methods in the art can be used to develop procedures to isolate it from cell lysates or the media. See, e.g., Scopes, R K (1994) Protein Purification: Principles and Practice, 3rd ed., New York: Springer-Verlag.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications cited herein, are hereby incorporated by reference in their entirety.

Vectors Encoding Truncated 1,3-1,4-β-D-Glucanase 1. pPCR-TF-Glucanase

A nucleic acid was amplified from the full-length *Fibrobacter succinogenes* 1,3-1,4-β-D-glucanase (Fsβ-D-glucanase) cDNA (Chen et al. (2001), J. Biol. Chem. 276, 17895-17901) by the PCR using the following two primers: Oligo A: 5'-CAGCCGGCGATGGCCATGGTTAGC GCA-3' (SEQ ID NO: 17) and Oligo B: 5'-CTGCTAGAAGAATTCGGAG-CAGGTTCGTC-3' (SEQ ID NO: 18). The amplified nucleic acid encodes a polypeptide that corresponds to a fragment from aa 24 to 272 of SEQ ID NO: 1, except that the N24 was replaced with M. The polypeptide lacks the C-terminal 78 aa of Fsβ-D-glucanase. To generate an expression vector, the amplified nucleic acid was digested with Nco I and Eco RI and then ligated into a pET26b(+) vector (NOVAGEN, WI) that had been digested with the same enzymes. The resultant vector was confirmed by DNA sequencing. This construct, designated as pPCR-TF-glucanase, encodes a fusion protein (SEQ ID NO: 10) that has a pel B leading peptide sequence (KYLLPTAAAGLLLLAAQPAMA, SEQ ID NO: 11) at the N-terminus and a 19-residue segment (SEQ ID NO: 16) at the C-terminus. Once expressed in a host cell, the pel B leading peptide sequence was cleaved to generate a mature fusion truncated glucanase, PCR-TF-glucanase (SEQ ID NO: 9).

Another truncated Fsβ-D-glucanase (SEQ ID NO: 7), designated as "TF-glucanase," was created using PCR-based site-directed mutagenesis. This TF-glucanase lacks the just-described 19-residue segment at its C-terminus. To make a nucleic acid encoding it, a stop codon was introduced right after the codon for P248 of the just-described pPCR-TF-glucanase. A pair of complementary mutagenic primers were used. The sense strand primer has the sequence: 5'-CCT-GCTCCGTAATCGAGCTCC-3' (SEQ ID NO: 19). The mutagenesis was carried out in a PCR reaction mixture containing 10 mM KCl, 10 mM $(NH_4)_2SO_4$, 20 mM Tris-HCl (pH 8.8), 2 mM $MgCl_2$, 0.1% Triton$^R$ X-100, 0.1 mg/ml nucleasefree BSA, 10-15 ng of template DNA, 0.2 mM dNTPs, 0.25 µM each of the primers, and 2.5 units of Turbo Pfu DNA polymerase (STRATAGENE, La Jolla, Calif.). The PCR reactions were conducted on a Hybaid TouchDown thermal cycler using the following program: 2 min at 95° C., 16 cycles of 1 min at 55° C./13 min at 68° C./45 sec at 95° C. The products were digested with 10 units of Dpn I at 37° C. for 1 hour (h) and subsequently transformed into *E. coli* XL-1 Blue competent cells by electroporation. The transformed cells were grown on LB agar plates containing 30 µg/ml kanamycin at 37° C. until colonies appeared on the plates. The colonies were selected randomly and cultured in 5 ml LB/kanamycin liquid culture at 37° C. for 16 h before plasmids were isolated from the culture using a QIAPREP Spin Miniprep kit (QIAGENE, Hilden, Germany). Mutation was confirmed by DNA sequencing. The plasmid thus obtained was named "pTF-glucanase."

3. pPCR-TF-W203F

A vector encoding a truncated glucanase having a Trp203→Phe (W203F) point mutation was generated by PCR based site-directed mutagenesis using the above described pPCR-TF-glucanase as the template in the same manner described above. A pair of complementary mutagenic primers were used. The sense strand primer was 5'-CTGGGGCAAGGGTGACTTCACATTTGACGGT-3' (SEQ ID NO: 20). The vector was augmented and prepared from *E. coli* XL-1 Blue, and confirmed by DNA sequencing. The vector and the polypeptide it encodes were designated as pPCR-TF-W203F and PCR-TF-W203F, respectively.

4. pPICZ-TFGlu

A *Pichia* expression vector that encodes a truncated glucanase was generated. Briefly, PCR was used to amplify the DNA sequence encoding V25 to P271 of SEQ ID NO: 1 from pPCR-TF-glucanase. The primers used were listed below:

```
Oligo C 5'-TACGCTGCAGTTAGCGCAAAGGATTTTAGC-3'     (SEQ ID NO: 21)
and

Oligo D 5'-TAGTTCTA GATCACGGAGCAGGTTCGTCATCTCTC-3'.  (SEQ ID NO: 22)
```

The PCR products were digested with PstI and XbaI and ligated into a *Pichia* expression vector, pPICZαB (INVITROGEN, CA, USA), which had been digested with the same enzymes. This vector, designated as pPICZ-TFGlu, encodes a truncated glucanase that is fused to an α factor signal sequence at its N-terminus. Once expressed in *Pichia*, the signal sequence allows the TF-glucanase to be secreted into culture medium.

Expression of Truncated Glucanase in *E. coli*

Each of the above described pET26b (+) series plasmids was transformed into BL21 (DE3) bacteria. Five ml of pre-grown culture of the bacteria were inoculated into 500 ml of fresh LB broth containing 30 µg/ml kanamycin and cultured at 33° C. until the OD600 nm reached 0.4-0.6. Then, 1 mM IPTG was added into the culture to induce the expression of TF-glucanase for 16 hours.

The supernatants were collected by centrifugation at 8,000×g for 15 min at 4° C. Their volumes were reduced by 10-fold on a Pellicon Cassette concentrator (MILLIPORE, Bedford, Mass.) using 10,000 $M_r$ cut-off membranes. The concentrated supernatants were then dialyzed against 50 mM Tris-HCl buffer, pH 7.8 (buffer A) and loaded onto a Sepharose Q FF (PHARMACIA, Sweden) column pre-equilibrated with the same buffer. TF-glucanases were eluted from the column with 0 to 1 M NaCl gradient in buffer A. The homogeneity of the purified enzyme was verified by SDS-polyacrylamide gel electrophoresis (SDS-PAGE). Protein concentration was determined according to the method described in Bradford M. (1976) Anal. Biochem. 72, 248-254. Bovine serum albumin (BSA) was used as the standard.

It was found that each of the E. coli expressed truncated glucanases (PCR-TF-glucanase, TF-glucanase, and PCR-TF-W203F) and full-length glucanases (Fsβ-D-glucanase) was a single polypeptide and that more than 85% of each enzyme is soluble in the medium. It was also observed that, after 16 hours of IPTG induction, there were $2.2 \times 10^5$ U truncated enzyme/liter of medium. Homogeneous wild-type and truncated glucanase were obtained using Ni-NTA affinity columns. The purities of the enzymes were found to be greater than 96% by SDS-PAGE and zymogram analyses.

Expression of Truncated Glucanase in Pichia pastoris

TF glucanase was expressed in P. pastoris strain X-33 using the Pichia expression kit (INVITROGEN) according to the manufacturer's instructions. Briefly, a starting culture of X-33 containing the above-described pPICZ-TFGlu was grown in 25 ml of BMGY medium (1% yeast extract, 2% peptone, 100 mM potassium phosphate, pH 6.0, 1.34% yeast nitrogen base, $4 \times 10^{-5}$% (w/v) biotin, and 1% glycerol) at 28° C. overnight.

The overnight culture was centrifuged at 3000×g for 5 min at room temperature, and the cell pellet resuspended in a BMMY medium containing 0.5% (v/v) methanol instead of 1% glycerol. The OD600 nm of the resultant culture was 1.0. 100 ml of this culture was transferred into a 1-liter baffled flask and cultured at 28° C. while being shaken at 250 rpm. Methanol (0.5%) was added into the culture every 24 hours.

One milliliter sample was taken from the culture at 1-2 day intervals to evaluate the yield and enzymatic activity of the expressed TF glucanase. This sample was centrifuged, and the supernatant was evaluated by zymograms according to the method described in Piruzian et al., Mol Gen Genet. 1998 March; 257(5):561-7. Briefly, lichenan (1 mg/ml) and the supernatant were mixed in a sample buffer (Laemmli, (1970) Nature. 227, 680-685) and heated at 90° C. for 10 min before being subjected to 12% SDS-PAGE. The gel was rinsed twice with 20% isopropanol-50 mM sodium citrate buffer (pH 6.0) for 20 min to remove SDS, and equilibrated in 50 mM sodium citrate buffer for 20 min. After the gel was incubated at 40° C. for 10 min, it was stained with Congo red solution (0.5 mg/ml) to visualize protein, which exhibits 1,3-1,4-β-D-glucanase activity.

1,3-1,4-β-D-glucanase enzymatic activity was also determined by measuring the rate of reducing sugar production from the hydrolysis of lichenan or barley β-glucan. Reducing sugar was measured and quantified according to the method described in Miller (1959) Anal. Chem. 31, 426-428 using glucose as the standard. Briefly, 2.7~8 mg/ml lichenan was incubated with the expressed enzyme in a 0.3 ml 50 mM sodium citrate buffer (pH 6.0) at 50° C. for 10 min. 40 μg/ml Bacillus subtilis lichenase (MEGAZYME, Ireland) was used as a reference control. The reaction was terminated by the addition of salicylic acid solution. Data were analyzed using the computer program ENZFITTER (BIOSOFT, USA) and Enzyme Kinetics (SigmaPlot 2000, SPSS Inc.) Data were analyzed using the computer program ENZFITTER (BIOSOFT, USA) and Enzyme Kinetics (SIGMAPLOT 2000, SPSS Inc.) One unit (U) of enzyme activity was defined as the amount of enzyme required to release one μmol of reducing sugar (e.g., glucose equivalent) per minute. The activity was expressed in μmoles of glucose per minute per milligram of protein.

The result showed that cell density ($OD_{600}$) of P. pastoris increased quickly during the first 2-3 days and reached a plateau around day 10. The amount of TF-glucanase in the culture medium increased quickly in the first 2 days and in days 8-14, and reached a plateau after day 15. The enzymatic activity of the TF-glucanase ($OD_{575}$), determined by the standard activity assay described above, was approximately $1.94 \times 10^6$ U/427 mg/L and $1.76 \times 10^6$ U/469 mg/L at day 15 and 23, respectively.

SDS-PAGE was carried out and showed that that more than 90% of the TF-glucanase existed as two dominant glycosylated forms. Homogeneous glycosylated TF-glucanase (>96% purity) was obtained using Q-anion ion exchange column chromatography. The glycoside moiety of the glycosylated-TF-glucanase could be removed after digestion with glycosidases using the Enzymatic Deglycosylation Kit (BIO-RAD). The resultant single band of the P. pastoris-expressed TF-glucanase had mobility on SDS gel similar to that of the E. coli.-expressed TF-glucanase Biochemical Characterization of Fsβ-Glucanase The N-terminus first 25 amino acid residues of the bacterial-expressed Fsβ-glucanase and truncated glucanases were sequenced and found to be correct. The glucanases did not contain pel B leader peptide at their N-termini, indicating that leader peptide was cleaved off in E. coli cells.

Electrospray ionization-tandem mass spectrometry was carried out to determined the molecular mass of the above-described glucanases. 10 nmole of protein sample was analyzed on a LCQ (FINNIGAN LCQ, USA) ion trap mass spectrometer operated in full-scan MS mode (400.00-2000.00). The molecular masses of Fsβ-glucanases, the two glycosylated forms of TF-glucanases, the deglycosylated TF-glucanase were found to be 37,669, 31,850, 29,983, and 27,957 Da, respectively. These results indicate that the two glycosylated glucanases consisted of 24 and 12 glycosides, respectively. The E. coli-expressed PCR-TF-glucanase and TF-glucanase were also examined and found to have molecular weights of 29,722 and 27,744 Da, respectively.

Kinetic Properties of Truncated-Glucanases Produced from E. coli and Pichia Host Cells The enzymatic activities of Fsβ-glucanase, TF-glucanase, PCR-TF-glucanase, PCR-TF-W203F, Glycosylated TF-Glucanase, and Lichanase (MEGAZYME, Ireland) were determined by the lichenan-hydrolysis assay described above. The results are shown in Table 1 below.

TABLE 1

Kinetic properties of various glucanases and Lichanase

| Enzyme | Activity (U/mg) | $k_{cat}$ ($^{-1}$s) | Opt. Temp. (° C.) | Opt pH |
|---|---|---|---|---|
| Fsβ-glucanase[a] | 2065 ± 82 | 1296 ± 51 | 50 (at pH 6.0) | 6.0-8.0 |
| PCR-TF-Glucanase[a] | 7833 ± 334 | 3911 ± 166 | 50 (at pH 6.0) | 6.0-8.0 |
| PCR-TF-W203F[a] | 13238 ± 624 | 6619 ± 312 | 50 (at pH 6.0) | 6.0-8.0 |
| TF-Glucanase[a] | 7980 ± 341 | 3695 ± 157 | 50 (at pH 6.0) | 6.0-8.0 |
| Glycosylated TF-Glucanase[a] | 10831 ± 185 | 5365 ± 92 | 50 (at pH 6.0) | 6.0-7.0 |

TABLE 1-continued

Kinetic properties of various glucanases and Lichanase

| Enzyme | Activity (U/mg) | $k_{cat}(^{-1}s)$ | Opt. Temp. (° C.) | Opt pH |
|---|---|---|---|---|
| Lichanase (Megazyme) | 118[b]<br>82.6 ± 0.96[c] | 47.2[b]<br>33.0 ± 0.38[c] | 60 (at pH 6.5)[b]<br>55 (at pH 7.0)[c] | 6.5-7.0[b] |

[a]The kinetics for each truncated glucanase was performed using lichenan as the substrate in 50 mM citrate buffer (pH 6.0);
[b]Data were taken from the manufacturer's instruction brochure and lichenan was used as the substrate
[c]Barley β-glucan was used as the substrate in 50 mM phosphate buffer (pH 7.0).

As shown in Table 1, *E. coli*-expressed PCR-TF-glucanase and TF-glucanase and *Pichia*-expressed glycosylated TF-glucanase require similar conditions for optimal enzymatic activity, i.e., 50° C. and pH 5-9. The activities of PCR-TF-glucanase and TF-glucanase are higher than that of Fsβ-glucanase by approximately 3.9-fold. The activity of PCR-TF-W203F was higher than those of PCR-TF-glucanase and TF-glucanase by about 1.69-fold. These results indicate that the W203F mutation increases the enzymatic activity.

Further, the specific activity and turnover rate $k_{cat}$ of glycosylated TF-glucanase were higher than that of TF-glucanase or PCR-TF-glucanase by 1.36-fold. These results indicate that the post-translational modification of TF-glucanase, e.g., glycosylation, does not compromise the protein structure or catalytic activity, but enhances the catalytic activity The kinetic properties of glycosylated TF glucanase were compared with those of other known glucanases. The data are summarized in Table 2 below:

CD Spectrometric Analysis

Circular dichroism (CD) spectrometry was performed to determine the melting points of the full length and truncated forms of 1,3-1,4-β-D-glucanases. This analysis was carried out in a Jasco J715 CD spectrometer and a 1-mm cell at 25° C. Spectra were collected from 200 to 260 nm in 1.3-nm increments, and each spectrum was blank-collected and smoothed using the software package provided by the manufacturer.

$CD_{224\ nm}$ signals of Fsβ-glucanase and each of the above-described truncated glucanases were monitored in temperatures ranging from 25-70° C. $CD_{224\ nm}(F_{app})$, representing the apparent fraction on native protein, was calculated as follows: $F_{app}=(Y_{obsd}-Y_U)/(Y_N-Y_U)$ (Cai et al., (1996) J. Biol. Chem. 271, 2987-2994.). $Y_{obsd}$ represents the observed value of $CD_{224\ nm}$ of each enzyme at various temperatures. $Y_N$ and $Y_U$ represent the CD values at 224 nm of each enzyme at 25° C. and 70° C., respectively. Similar melting points (47 to

TABLE 2

Comparison of kinetic properties of various 1,3-1,4-β-D-glucanases

| Enzyme (Organism/source) | Specific Activity (units/mg) | $k_{cat}(s^{-1})$ | Temperature Optima (° C.) | PH Optima |
|---|---|---|---|---|
| Glycosylated-TF-Glucanase[a] | 10831 ± 185 | 5365 ± 92 | 50 | 6.0-7.0 |
| Orpinomyces strain PC-2[b] | 3790 (lichenan)<br>5320 (barley glucan) | 1764<br>2476 | 45 | ~6.0 |
| *B. macerans*[c] | — | 1880 ± 70 (at 50° C.) | 65 | 7.0 |
| H(A16-M)[c] | 3731 ± 91<br>4890 ± 120 | 1860 ± 50 (at 50° C.)<br>2445 ± 60 (at 64° C.) | 64 | 6.5-7.0 |
| CPA16M-59[c] | 2833 ± 69<br>3930 ± 100 | 1450 ± 90 (at 50° C.)<br>2015 ± 51 (at 62° C.) | 62 | 6.5-6.8 |
| *C. thermocellum*[d] | 214 | 135 | 80 | 8-9 |
| *B. subtilis*[e] | 2600 | 1101 | 55 | 6.5 |
| *B. licheniformis*[f] | 900 ± 60 | 411 ± 27 | 55 | 7.0 |
| *B. amyloliquefaciens*[g] | 2490 | 1077 | 55 | 6.5 |
| Lichenase (Megazyme)[i] | 118 | | 60 | 6.5-7.0 |

[a]Data from Table 1
[b]Chen et al. J. Bacteriol. 179, 6028-6034
[c]Hahn et al. Proc. Natl. Acad. Sci. USA 91, 10417-10421 and Ay et al. PROTEINS: Structure, Function, and Genetics 30, 155-167
[d]Schimming et al. Eur. J. Biochem. 204, 13-19
[e]Tezuka et al. Agric. Biol. Chem. 53, 2335-2339
[f]Lloberas et al. Eur. J. Biochem. 197, 337-343
[g]Hofemeister et al. Gene 49(2), 177-187
[i]Megazyme brochure As showing in Table 3, glycosylated TF-glucanase has a much higher catalytic activity and better heat-tolerance than the other glucanases.

48° C.) were observed for all of the enzymes. These results suggest that Fsβ-glucanase and the truncated glucanases have similar structural folding.

Sensitivity to Trypsin Digestion and pH Changes

Each of the above described purified full-length glucanase, glycosylated TF-glucanase, and non-glycosylated glucanase was incubated with trypsin (1 mg/mL)-50 mM phosphate buffer (pH 7.0) at 37° C. for 1, 2.5, and 5 hours, respectively. The enzymatic activity of each enzyme was determined using standard assay before and after the trypsin digestion. It was found that all three glucanases exhibited similar resistance to trypsin digestion. For example, after 5 hours of digestion, all of the enzymes retained more than 60% of their original activities. These results indicate that the truncation of *F. succinogenes* 1,3-1,4-β-glucanase does not affect the resistance to trypsin digestion.

Each of the full-length glucanase, glycosylated TF-glucanase, and non-glycosylated TF glucanase were incubated in buffers having pH ranging from 2 to 10 for one hour, respectively. The activities of the four enzymes were then examined in the same manner described above. It was found that the activities decreased by 30~38% after the enzymes were incubated in a 50 mM sodium acetate buffer (pH 4.0). After incubation in buffers having pH of 6, 7, 8, 9, or 0, the enzymes retained more than 90% of their enzymatic activities. These results indicate that the truncation of the β-glucanase does not affect the resistance to changes in environment pH.

Reactivation of TF-Glucanase After Heat Treatment

Fsβ-glucanase and TF-glucanase were heated at 90° C. for 10 minutes, transferred to room temperature (25° C.) immediately, and recovered at this temperature for up to 24 hours. At various time points, the activities of the enzymes were examined by a standard assay. At minute 3 after the heat treatment, Fsβ-glucanase and TF-glucanases resumed 8% and 40% of their original activities, respectively. At minute 12, they resumed 27% and 80% of the original activities. At hour 4, they retained 10% and 90% of their original activities. At hour 6 and thereafter, Fsβ-glucanase almost lost all activity. In contrast, TF-glucanase still had 70% of its original activity.

A *Bacillus* lichenase (MEGAZYME) was also examined and was found to be more heat-sensitive than TF-glucanase. After being heated at 90° C. for 10 minute, its activity was hardly restored (<10%) after recovering for 3 minutes to 2 hours, and was lost completely after recovering for 4 to 6 hours.

In another experiment, *E. coli* expressed-TF-glucanase ("TF-glucanase") and *Pichia*-expressed glycosylated TF-glicanase ("Glycosylated TF-glucanase") were heated at 90° C. or 100° C. for 10 or 30 minutes, and recovered at 25° C. for 10 or 20 minutes. The recovery of their activities was studied in the same manner described above. The results are summarized in Table 3 below.

TABLE 3

Reactivation of TF-glucanase after heat treatment

| Treatment | Recovery Time (min) | TF-glucanase Relative activity (%) | Glycosylated TF-glucanase Relative activity (%) |
|---|---|---|---|
| None | — | 100 | 100 |
| 90° C., 10 min | 10 | 68 | 79 |
|  | 20 | 81 | 86 |
| 90° C., 30 min | 10 | 61 | 82 |
|  | 20 | 67 | 89 |
| 100° C., 10 min | 10 | 68 | 83 |
|  | 20 | 72 | 88 |
| 100° C., 30 min | 10 | 55 | 61 |
|  | 20 | 56 | 66 |

As shown in Table 3, the enzymes retained at least 55% of their original activities. The glycosylated TF-glucanase exhibited a reactivation profile similar to that of TF-glucanase. Unexpectedly, it retained much higher enzymatic activity than the *E. coli*-expressed TF glucanase. For example, after being heated at 90° C. for 30 minutes and recovering for 20 minutes, the glycosylated TF-glucanase retained 89% of its activity, while TF-glucanase retained only 67% activity. After being heated at 100° C. for 10 and 30 minutes and recovering for 20 minutes, the glycosylated enzyme recovered 88% and 66% of its activity, respectively. In contrast, TF-glucanase only recovered 72% and 56% of their enzymatic activities. PCR-TF-glucanase was also examined and exhibited a profile similar to that of TF-glucanase. These results indicate that a glycosylated glucanase is more resistant to heat.

Fluorescence Spectrometric Analysis of Wild Type and Truncated Fsβ-Glucanases

The structural integrity of native, heat-denatured, and denatured-recovered wild type and PCR-TF-glucanases were analyzed using fluorescence spectrometry. Enzyme samples (0.03 mg/mi in 50 mM sodium phosphate, pH 7.0) were heated at 90° C. and recovered at 25° C. for 0, 3, and 10 min, respectively. Their spectra from 305 nm to 430 nm of fluorescence emission excited by 295 nm light were recorded on an AMICO-Bowman Series 2 spectrofluorimeter (SPECTRONIC INSTRUMENTS, Inc., NY) at 25° C. with a 1×1-cm cuvette. A 4-nm slit was used for the recordation.

It was found that the emission spectra of the native full-length and truncated enzymes had emission peaks at 335 nm. After heating at 90° C. for 10 min and recovering at 25° C. for 3 or 10 min, the emission spectrum of the wild type enzyme did not superimpose with that of the unheated wild type enzyme. In contrast, the emission spectrum of the heated PCR-TF-glucanase was superimposed with that of the native PCR-TF-glucanase enzyme after recovering for 3 to 10 minutes at 25° C. These results are consistent with the enzymatic activities of the wild type and truncated glucanases before and after the heating-recovering process.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. An isolated polypeptide comprising the enzymatic catalytic domains of 1,3-1,4-β-D-glucanase and excluding the carboxyl terminal 78 amino acid residues of the 1,3-1,4-β-D-glucanase, wherein the 1,3-1,4-β-D-glucanase is a wild type 1,3-1,4-β-D-glucanase having SEQ ID NO: 1 and wherein the isolated polypeptide has a higher enzymatic activity than the wild type 1,3-1,4-β-D-glucanase, and wherein one of the catalytic domains includes the sequence of SEQ ID NO: 3 or 4.

2. The polypeptide of claim 1, wherein the polypeptide contains the sequence of SEQ ID NO: 7.

3. The polypeptide of claim 2, wherein the polypeptide contains the sequence of SEQ ID NO: 12.

4. An isolated polypeptide comprising the sequence of SEQ ID NO: 8 and excluding the carboxyl terminal 78 amino acid residues of SEQ ID NO: 1 wherein the isolated polypeptide has a higher enzymatic activity than a wild type 1,3-1,4-β-D-glucanase having the sequence of SEQ ID NO: 1.

5. The polypeptide of claim 4, wherein the polypeptide contains the sequence of SEQ ID NO: 12.

6. The polypeptide of claim 5, wherein the polypeptide contains the sequence of SEQ ID NO: 13 or 15.

7. The polypeptide of claim 1, wherein the polypeptide is glycosylated.

8. The polypeptide of claim 7, wherein the polypeptide contains the sequence of SEQ ID NO: 7.

9. The polypeptide of claim 8, wherein the polypeptide contains the sequence of SEQ ID NO: 12.

10. The polypeptide of claim 4, wherein the polypeptide is glycosylated.

11. The polypeptide of claim 10, wherein the polypeptide contains the sequence of SEQ ID NO: 12.

12. The polypeptide of claim 11, wherein the polypeptide contains the sequence of SEQ ID NO: 13 or 15.

13. The isolated polypeptide of claim 1, wherein the enzymatic catalytic domains include SEQ ID NOs: 3 and 4.

* * * * *

SEQUENCE LISTING

<160> NUMBER OF SEQ ID NOS: 22

<210> SEQ ID NO 1
<211> LENGTH: 349
<212> TYPE: PRT
<213> ORGANISM: Fibrobacter succinogenes

<400> SEQUENCE: 1

```
Met Asn Ile Lys Lys Thr Ala Val Lys Ser Ala Leu Ala Val Ala Ala
 1               5                  10                  15

Ala Ala Ala Ala Leu Thr Thr Asn Val Ser Ala Lys Asp Phe Ser Gly
                20                  25                  30

Ala Glu Leu Tyr Thr Leu Glu Glu Val Gln Tyr Gly Lys Phe Glu Ala
            35                  40                  45

Arg Met Lys Met Ala Ala Ala Ser Gly Thr Val Ser Ser Met Phe Leu
50                  55                  60

Tyr Gln Asn Gly Ser Glu Ile Ala Asp Gly Arg Pro Trp Val Glu Val
65                  70                  75                  80

Asp Ile Glu Val Leu Gly Lys Asn Pro Gly Ser Phe Gln Ser Asn Ile
                85                  90                  95

Ile Thr Gly Lys Ala Gly Ala Gln Lys Thr Ser Glu Lys His His Ala
            100                 105                 110

Val Ser Pro Ala Ala Asp Gln Ala Phe His Thr Tyr Gly Leu Glu Trp
        115                 120                 125

Thr Pro Asn Tyr Val Arg Trp Thr Val Asp Gly Gln Glu Val Arg Lys
    130                 135                 140

Thr Glu Gly Gly Gln Val Ser Asn Leu Thr Gly Thr Gln Gly Leu Arg
145                 150                 155                 160

Phe Asn Leu Trp Ser Ser Glu Ser Ala Ala Trp Val Gly Gln Phe Asp
                165                 170                 175

Glu Ser Lys Leu Pro Leu Phe Gln Phe Ile Asn Trp Val Lys Val Tyr
            180                 185                 190

Lys Tyr Thr Pro Gly Gln Gly Gly Gly Ser Asp Phe Thr Leu Asp
        195                 200                 205

Trp Thr Asp Asn Phe Asp Thr Phe Asp Gly Ser Arg Trp Gly Lys Gly
    210                 215                 220

Asp Trp Thr Phe Asp Gly Asn Arg Val Asp Leu Thr Asp Lys Asn Ile
225                 230                 235                 240

Tyr Ser Arg Asp Gly Met Leu Ile Leu Ala Leu Thr Arg Lys Gly Gln
                245                 250                 255

Glu Ser Phe Asn Gly Gln Val Pro Arg Asp Asp Glu Pro Ala Pro Gln
            260                 265                 270

Ser Ser Ser Ser Ala Pro Ala Ser Ser Ser Val Pro Ala Ser Ser
        275                 280                 285

Ser Ser Val Pro Ala Ser Ser Ser Ala Phe Val Pro Pro Ser Ser
    290                 295                 300

Ser Ser Ala Thr Asn Ala Ile His Gly Met Arg Thr Thr Pro Ala Val
305                 310                 315                 320

Ala Lys Glu His Arg Asn Leu Val Asn Ala Lys Gly Ala Lys Val Asn
                325                 330                 335

Pro Asn Gly His Lys Arg Tyr Arg Val Asn Phe Glu His
            340                 345
```

```
<210> SEQ ID NO 2
<211> LENGTH: 27
<212> TYPE: PRT
<213> ORGANISM: Fibrobacter succinogenes

<400> SEQUENCE: 2

Met Asn Ile Lys Lys Thr Ala Val Lys Ser Ala Leu Ala Val Ala Ala
1               5                   10                  15

Ala Ala Ala Ala Leu Thr Thr Asn Val Ser Ala
            20                  25

<210> SEQ ID NO 3
<211> LENGTH: 175
<212> TYPE: PRT
<213> ORGANISM: Fibrobacter succinogenes

<400> SEQUENCE: 3

Lys Asp Phe Ser Gly Ala Glu Leu Tyr Thr Leu Glu Glu Val Gln Tyr
1               5                   10                  15

Gly Lys Phe Glu Ala Arg Met Lys Met Ala Ala Ala Ser Gly Thr Val
            20                  25                  30

Ser Ser Met Phe Leu Tyr Gln Asn Gly Ser Glu Ile Ala Asp Gly Arg
        35                  40                  45

Pro Trp Val Glu Val Asp Ile Glu Val Leu Gly Lys Asn Pro Gly Ser
    50                  55                  60

Phe Gln Ser Asn Ile Ile Thr Gly Lys Ala Gly Ala Gln Lys Thr Ser
65                  70                  75                  80

Glu Lys His His Ala Val Ser Pro Ala Ala Asp Gln Ala Phe His Thr
                85                  90                  95

Tyr Gly Leu Glu Trp Thr Pro Asn Tyr Val Arg Trp Thr Val Asp Gly
            100                 105                 110

Gln Glu Val Arg Lys Thr Glu Gly Gln Val Ser Asn Leu Thr Gly
        115                 120                 125

Thr Gln Gly Leu Arg Phe Asn Leu Trp Ser Ser Glu Ser Ala Ala Trp
    130                 135                 140

Val Gly Gln Phe Asp Glu Ser Lys Leu Pro Leu Phe Gln Phe Ile Asn
145                 150                 155                 160

Trp Val Lys Val Tyr Lys Tyr Thr Pro Gly Gln Gly Glu Gly Gly
                165                 170                 175

<210> SEQ ID NO 4
<211> LENGTH: 64
<212> TYPE: PRT
<213> ORGANISM: Fibrobacter succinogenes

<400> SEQUENCE: 4

Ser Asp Phe Thr Leu Asp Trp Thr Asp Asn Phe Asp Thr Phe Asp Gly
1               5                   10                  15

Ser Arg Trp Gly Lys Gly Asp Trp Thr Phe Asp Gly Asn Arg Val Asp
            20                  25                  30

Leu Thr Asp Lys Asn Ile Tyr Ser Arg Asp Gly Met Leu Ile Leu Ala
        35                  40                  45

Leu Thr Arg Lys Gly Gln Glu Ser Phe Asn Gly Gln Val Pro Arg Asp
    50                  55                  60

<210> SEQ ID NO 5
<211> LENGTH: 78
<212> TYPE: PRT
<213> ORGANISM: Fibrobacter succinogenes
```

-continued

<400> SEQUENCE: 5

```
Gln Ser Ser Ser Ala Pro Ala Ser Ser Ser Val Pro Ala Ser
1               5                   10                  15

Ser Ser Ser Val Pro Ala Ser Ser Ser Ala Phe Val Pro Pro Ser
            20                  25                  30

Ser Ser Ser Ala Thr Asn Ala Ile His Gly Met Arg Thr Thr Pro Ala
            35                  40                  45

Val Ala Lys Glu His Arg Asn Leu Val Asn Ala Lys Gly Ala Lys Val
    50                  55                  60

Asn Pro Asn Gly His Lys Arg Tyr Arg Val Asn Phe Glu His
65                  70                  75
```

<210> SEQ ID NO 6
<211> LENGTH: 1050
<212> TYPE: DNA
<213> ORGANISM: Fibrobacter succinogenes
<220> FEATURE:
<221> NAME/KEY: CDS
<222> LOCATION: (1)...(1047)

<400> SEQUENCE: 6

| | |
|---|---:|
| atg aac atc aag aaa act gca gtc aag agc gct ctc gcc gta gca gcc<br>Met Asn Ile Lys Lys Thr Ala Val Lys Ser Ala Leu Ala Val Ala Ala<br>1               5                 10               15 | 48 |
| gca gca gca gcc ctc acc acc aat gtt agc gca aag gat ttt agc ggt<br>Ala Ala Ala Ala Leu Thr Thr Asn Val Ser Ala Lys Asp Phe Ser Gly<br>               20               25               30 | 96 |
| gcc gaa ctc tac acg tta gaa gaa gtt cag tac ggt aag ttt gaa gcc<br>Ala Glu Leu Tyr Thr Leu Glu Glu Val Gln Tyr Gly Lys Phe Glu Ala<br>               35               40               45 | 144 |
| cgt atg aag atg gca gcc gca tcg gga aca gtc agt tcc atg ttc ctc<br>Arg Met Lys Met Ala Ala Ala Ser Gly Thr Val Ser Ser Met Phe Leu<br>       50                55               60 | 192 |
| tac cag aat ggt tcc gaa atc gcc gat gga agg ccc tgg gta gaa gtg<br>Tyr Gln Asn Gly Ser Glu Ile Ala Asp Gly Arg Pro Trp Val Glu Val<br>65               70               75               80 | 240 |
| gat att gaa gtt ctc ggc aag aat ccg ggc agt ttc cag tcc aac atc<br>Asp Ile Glu Val Leu Gly Lys Asn Pro Gly Ser Phe Gln Ser Asn Ile<br>               85               90               95 | 288 |
| att acc ggt aag gcc ggc gca caa aag act agc gaa aag cac cat gct<br>Ile Thr Gly Lys Ala Gly Ala Gln Lys Thr Ser Glu Lys His His Ala<br>               100             105             110 | 336 |
| gtt agc ccc gcc gcc gat cag gct ttc cac acc tac ggt ctc gaa tgg<br>Val Ser Pro Ala Ala Asp Gln Ala Phe His Thr Tyr Gly Leu Glu Trp<br>       115                120               125 | 384 |
| act ccg aat tac gtc cgc tgg act gtt gac ggt cag gaa gtc cgc aag<br>Thr Pro Asn Tyr Val Arg Trp Thr Val Asp Gly Gln Glu Val Arg Lys<br>       130                135               140 | 432 |
| acg gaa ggt ggc cag gtt tcc aac ttg aca ggt aca cag gga ctc cgt<br>Thr Glu Gly Gly Gln Val Ser Asn Leu Thr Gly Thr Gln Gly Leu Arg<br>145               150               155               160 | 480 |
| ttt aac ctt tgg tcg tct gag agt gcg gct tgg gtt ggc cag ttc gat<br>Phe Asn Leu Trp Ser Ser Glu Ser Ala Ala Trp Val Gly Gln Phe Asp<br>               165             170             175 | 528 |
| gaa tca aag ctt ccg ctt ttc cag ttc atc aac tgg gtc aag gtt tat<br>Glu Ser Lys Leu Pro Leu Phe Gln Phe Ile Asn Trp Val Lys Val Tyr<br>       180                185               190 | 576 |
| aag tat acg ccg ggc cag ggc gaa ggc ggc agc gac ttt acg ctt gac<br>Lys Tyr Thr Pro Gly Gln Gly Glu Gly Gly Ser Asp Phe Thr Leu Asp | 624 |

```
                195                 200                 205
tgg acc gac aat ttt gac acg ttt gat ggc tcc cgc tgg ggc aag ggt         672
Trp Thr Asp Asn Phe Asp Thr Phe Asp Gly Ser Arg Trp Gly Lys Gly
    210                 215                 220 gac tgg aca ttt gac ggt aac cgt gtc gac ctc acc gac aag aac atc         720
Asp Trp Thr Phe Asp Gly Asn Arg Val Asp Leu Thr Asp Lys Asn Ile
225                 230                 235                 240 tac tcc aga gat ggc atg ttg atc ctc gcc ctc acc cgc aaa ggt cag         768
Tyr Ser Arg Asp Gly Met Leu Ile Leu Ala Leu Thr Arg Lys Gly Gln
                245                 250                 255 gaa agc ttc aac ggc cag gtt ccg aga gat gac gaa cct gct ccg caa         816
Glu Ser Phe Asn Gly Gln Val Pro Arg Asp Asp Glu Pro Ala Pro Gln
            260                 265                 270 tct tct agc agc gct ccg gca tct tct agc agt gtt ccg gca agc tcc         864
Ser Ser Ser Ser Ala Pro Ala Ser Ser Ser Ser Val Pro Ala Ser Ser
        275                 280                 285 tct agc gtc cct gcc tcc tcg agc agc gca ttt gtt ccg ccg agc tcc         912
Ser Ser Val Pro Ala Ser Ser Ser Ala Phe Val Pro Pro Ser Ser
    290                 295                 300 tcg agc gcc aca aac gca atc cac gga atg cgc aca act ccg gca gtt         960
Ser Ser Ala Thr Asn Ala Ile His Gly Met Arg Thr Thr Pro Ala Val
305                 310                 315                 320 gca aag gaa cac cgc aat ctc gtg aac gcc aag ggt gcc aag gtg aac        1008
Ala Lys Glu His Arg Asn Leu Val Asn Ala Lys Gly Ala Lys Val Asn
                325                 330                 335 ccg aat ggc cac aag cgt tat cgc gtg aac ttt gaa cac taa                1050
Pro Asn Gly His Lys Arg Tyr Arg Val Asn Phe Glu His
                340                 345

<210> SEQ ID NO 7
<211> LENGTH: 248
<212> TYPE: PRT
<213> ORGANISM: Artificial Sequence
<220> FEATURE:
<223> OTHER INFORMATION: Synthetic construct

<400> SEQUENCE: 7

Met Val Ser Ala Lys Asp Phe Ser Gly Ala Glu Leu Tyr Thr Leu Glu
1               5                   10                  15

Glu Val Gln Tyr Gly Lys Phe Glu Ala Arg Met Lys Met Ala Ala
            20                  25                  30

Ser Gly Thr Val Ser Ser Met Phe Leu Tyr Gln Asn Gly Ser Glu Ile
        35                  40                  45

Ala Asp Gly Arg Pro Trp Val Glu Val Asp Ile Glu Val Leu Gly Lys
    50                  55                  60

Asn Pro Gly Ser Phe Gln Ser Asn Ile Ile Thr Gly Lys Ala Gly Ala
65                  70                  75                  80

Gln Lys Thr Ser Glu Lys His His Ala Val Ser Pro Ala Ala Asp Gln
                85                  90                  95

Ala Phe His Thr Tyr Gly Leu Glu Trp Thr Pro Asn Tyr Val Arg Trp
            100                 105                 110

Thr Val Asp Gly Gln Glu Val Arg Lys Thr Glu Gly Gln Val Ser
        115                 120                 125

Asn Leu Thr Gly Thr Gln Gly Leu Arg Phe Asn Leu Trp Ser Ser Glu
    130                 135                 140

Ser Ala Ala Trp Val Gly Gln Phe Asp Glu Ser Lys Leu Pro Leu Phe
145                 150                 155                 160

Gln Phe Ile Asn Trp Val Lys Val Tyr Lys Tyr Thr Pro Gly Gln Gly
```

```
                165                 170                 175
Glu Gly Gly Ser Asp Phe Thr Leu Asp Trp Thr Asp Asn Phe Asp Thr
                180                 185                 190

Phe Asp Gly Ser Arg Trp Gly Lys Gly Asp Trp Thr Phe Asp Gly Asn
            195                 200                 205

Arg Val Asp Leu Thr Asp Lys Asn Ile Tyr Ser Arg Asp Gly Met Leu
        210                 215                 220

Ile Leu Ala Leu Thr Arg Lys Gly Gln Glu Ser Phe Asn Gly Gln Val
225                 230                 235                 240

Pro Arg Asp Asp Glu Pro Ala Pro
                245

<210> SEQ ID NO 8
<211> LENGTH: 248
<212> TYPE: PRT
<213> ORGANISM: Artificial Sequence
<220> FEATURE:
<223> OTHER INFORMATION: Synthetic construct

<400> SEQUENCE: 8

Met Val Ser Ala Lys Asp Phe Ser Gly Ala Glu Leu Tyr Thr Leu Glu
1               5                   10                  15

Glu Val Gln Tyr Gly Lys Phe Glu Ala Arg Met Lys Met Ala Ala Ala
                20                  25                  30

Ser Gly Thr Val Ser Ser Met Phe Leu Tyr Gln Asn Gly Ser Glu Ile
            35                  40                  45

Ala Asp Gly Arg Pro Trp Val Glu Val Asp Ile Glu Val Leu Gly Lys
        50                  55                  60

Asn Pro Gly Ser Phe Gln Ser Asn Ile Ile Thr Gly Lys Ala Gly Ala
65                  70                  75                  80

Gln Lys Thr Ser Glu Lys His His Ala Val Ser Pro Ala Ala Asp Gln
                85                  90                  95

Ala Phe His Thr Tyr Gly Leu Glu Trp Thr Pro Asn Tyr Val Arg Trp
            100                 105                 110

Thr Val Asp Gly Gln Glu Val Arg Lys Thr Glu Gly Gly Gln Val Ser
        115                 120                 125

Asn Leu Thr Gly Thr Gln Gly Leu Arg Phe Asn Leu Trp Ser Ser Glu
    130                 135                 140

Ser Ala Ala Trp Val Gly Gln Phe Asp Glu Ser Lys Leu Pro Leu Phe
145                 150                 155                 160

Gln Phe Ile Asn Trp Val Lys Val Tyr Lys Tyr Thr Pro Gly Gln Gly
                165                 170                 175

Glu Gly Gly Ser Asp Phe Thr Leu Asp Trp Thr Asp Asn Phe Asp Thr
            180                 185                 190

Phe Asp Gly Ser Arg Trp Gly Lys Gly Asp Phe Thr Phe Asp Gly Asn
        195                 200                 205

Arg Val Asp Leu Thr Asp Lys Asn Ile Tyr Ser Arg Asp Gly Met Leu
    210                 215                 220

Ile Leu Ala Leu Thr Arg Lys Gly Gln Glu Ser Phe Asn Gly Gln Val
225                 230                 235                 240

Pro Arg Asp Asp Glu Pro Ala Pro
                245

<210> SEQ ID NO 9
<211> LENGTH: 257
<212> TYPE: PRT
```

<213> ORGANISM: Artificial Sequence
<220> FEATURE:
<223> OTHER INFORMATION: Fusion peptide

<400> SEQUENCE: 9

Met Val Ser Ala Lys Asp Phe Ser Gly Ala Glu Leu Tyr Thr Leu Glu
1               5                   10                  15

Glu Val Gln Tyr Gly Lys Phe Glu Ala Arg Met Lys Met Ala Ala Ala
            20                  25                  30

Ser Gly Thr Val Ser Ser Met Phe Leu Tyr Gln Asn Gly Ser Glu Ile
        35                  40                  45

Ala Asp Gly Arg Pro Trp Val Glu Val Asp Ile Glu Val Leu Gly Lys
    50                  55                  60

Asn Pro Gly Ser Phe Gln Ser Asn Ile Ile Thr Gly Lys Ala Gly Ala
65                  70                  75                  80

Gln Lys Thr Ser Glu Lys His His Ala Val Ser Pro Ala Ala Asp Gln
                85                  90                  95

Ala Phe His Thr Tyr Gly Leu Glu Trp Thr Pro Asn Tyr Val Arg Trp
            100                 105                 110

Thr Val Asp Gly Gln Glu Val Arg Lys Thr Glu Gly Gly Gln Val Ser
        115                 120                 125

Asn Leu Thr Gly Thr Gln Gly Leu Arg Phe Asn Leu Trp Ser Ser Glu
130                 135                 140

Ser Ala Ala Trp Val Gly Gln Phe Asp Glu Ser Lys Leu Pro Leu Phe
145                 150                 155                 160

Gln Phe Ile Asn Trp Val Lys Val Tyr Lys Tyr Thr Pro Gly Gln Gly
                165                 170                 175

Glu Gly Gly Ser Asp Phe Thr Leu Asp Trp Thr Asp Asn Phe Asp Thr
            180                 185                 190

Phe Asp Gly Ser Arg Trp Gly Lys Gly Asp Trp Thr Phe Asp Gly Asn
        195                 200                 205

Arg Val Asp Leu Thr Asp Lys Asn Ile Tyr Ser Arg Asp Gly Met Leu
    210                 215                 220

Ile Leu Ala Leu Thr Arg Lys Gly Gln Glu Ser Phe Asn Gly Gln Val
225                 230                 235                 240

Pro Arg Asp Asp Glu Pro Ala Pro Asn Ser Ser Val Asp Lys Leu Ala
                245                 250                 255

Ala

<210> SEQ ID NO 10
<211> LENGTH: 287
<212> TYPE: PRT
<213> ORGANISM: Artificial Sequence
<220> FEATURE:
<223> OTHER INFORMATION: Fusion peptide

<400> SEQUENCE: 10

Lys Tyr Leu Leu Pro Thr Ala Ala Ala Gly Leu Leu Leu Leu Ala Ala
1               5                   10                  15

Gln Pro Ala Met Ala Met Val Ser Ala Lys Asp Phe Ser Gly Ala Glu
            20                  25                  30

Leu Tyr Thr Leu Glu Glu Val Gln Tyr Gly Lys Phe Glu Ala Arg Met
        35                  40                  45

Lys Met Ala Ala Ala Ser Gly Thr Val Ser Ser Met Phe Leu Tyr Gln
    50                  55                  60

Asn Gly Ser Glu Ile Ala Asp Gly Arg Pro Trp Val Glu Val Asp Ile

```
                65                  70                  75                  80
Glu Val Leu Gly Lys Asn Pro Gly Ser Phe Gln Ser Asn Ile Ile Thr
                    85                  90                  95

Gly Lys Ala Gly Ala Gln Lys Thr Ser Glu Lys His His Ala Val Ser
                100                 105                 110

Pro Ala Ala Asp Gln Ala Phe His Thr Tyr Gly Leu Glu Trp Thr Pro
                115                 120                 125

Asn Tyr Val Arg Trp Thr Val Asp Gly Gln Glu Val Arg Lys Thr Glu
    130                 135                 140

Gly Gly Gln Val Ser Asn Leu Thr Gly Thr Gln Gly Leu Arg Phe Asn
145                 150                 155                 160

Leu Trp Ser Ser Glu Ser Ala Ala Trp Val Gly Gln Phe Asp Glu Ser
                165                 170                 175

Lys Leu Pro Leu Phe Gln Phe Ile Asn Trp Val Lys Val Tyr Lys Tyr
                180                 185                 190

Thr Pro Gly Gln Gly Glu Gly Gly Ser Asp Phe Thr Leu Asp Trp Thr
                195                 200                 205

Asp Asn Phe Asp Thr Phe Asp Gly Ser Arg Trp Gly Lys Gly Asp Trp
    210                 215                 220

Thr Phe Asp Gly Asn Arg Val Asp Leu Thr Asp Lys Asn Ile Tyr Ser
225                 230                 235                 240

Arg Asp Gly Met Leu Ile Leu Ala Leu Thr Arg Lys Gly Gln Glu Ser
                245                 250                 255

Phe Asn Gly Gln Val Pro Arg Asp Asp Glu Pro Ala Pro Asn Ser Ser
                260                 265                 270

Val Asp Lys Leu Ala Ala Ala Leu Glu His His His His His His
        275                 280                 285

<210> SEQ ID NO 11
<211> LENGTH: 21
<212> TYPE: PRT
<213> ORGANISM: Cloning vector pMAB136

<400> SEQUENCE: 11

Lys Tyr Leu Leu Pro Thr Ala Ala Ala Gly Leu Leu Leu Leu Ala Ala
1               5                   10                  15

Gln Pro Ala Met Ala
            20

<210> SEQ ID NO 12
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 12

Asn Ser Ser Val Asp Lys Leu Ala Ala
1               5

<210> SEQ ID NO 13
<211> LENGTH: 257
<212> TYPE: PRT
<213> ORGANISM: Artificial Sequence
<220> FEATURE:
<223> OTHER INFORMATION: Fusion peptide

<400> SEQUENCE: 13

Met Val Ser Ala Lys Asp Phe Ser Gly Ala Glu Leu Tyr Thr Leu Glu
```

```
                1               5                   10                  15
Glu Val Gln Tyr Gly Lys Phe Glu Ala Arg Met Lys Met Ala Ala Ala
                20                  25                  30

Ser Gly Thr Val Ser Ser Met Phe Leu Tyr Gln Asn Gly Ser Glu Ile
                35                  40                  45

Ala Asp Gly Arg Pro Trp Val Glu Val Asp Ile Glu Val Leu Gly Lys
 50                  55                  60

Asn Pro Gly Ser Phe Gln Ser Asn Ile Ile Thr Gly Lys Ala Gly Ala
 65                  70                  75                  80

Gln Lys Thr Ser Glu Lys His His Ala Val Ser Pro Ala Ala Asp Gln
                85                  90                  95

Ala Phe His Thr Tyr Gly Leu Glu Trp Thr Pro Asn Tyr Val Arg Trp
                100                 105                 110

Thr Val Asp Gly Gln Glu Val Arg Lys Thr Glu Gly Gly Gln Val Ser
                115                 120                 125

Asn Leu Thr Gly Thr Gln Gly Leu Arg Phe Asn Leu Trp Ser Ser Glu
                130                 135                 140

Ser Ala Ala Trp Val Gly Gln Phe Asp Glu Ser Lys Leu Pro Leu Phe
145                 150                 155                 160

Gln Phe Ile Asn Trp Val Lys Val Tyr Lys Tyr Thr Pro Gly Gln Gly
                165                 170                 175

Glu Gly Gly Ser Asp Phe Thr Leu Asp Trp Thr Asp Asn Phe Asp Thr
                180                 185                 190

Phe Asp Gly Ser Arg Trp Gly Lys Gly Asp Phe Thr Phe Asp Gly Asn
                195                 200                 205

Arg Val Asp Leu Thr Asp Lys Asn Ile Tyr Ser Arg Asp Gly Met Leu
                210                 215                 220

Ile Leu Ala Leu Thr Arg Lys Gly Gln Glu Ser Phe Asn Gly Gln Val
225                 230                 235                 240

Pro Arg Asp Asp Glu Pro Ala Pro Asn Ser Ser Val Asp Lys Leu Ala
                245                 250                 255

Ala
```

<210> SEQ ID NO 14
<211> LENGTH: 266
<212> TYPE: PRT
<213> ORGANISM: Artificial Sequence
<220> FEATURE:
<223> OTHER INFORMATION: Fusion peptide

<400> SEQUENCE: 14

```
Met Val Ser Ala Lys Asp Phe Ser Gly Ala Glu Leu Tyr Thr Leu Glu
 1               5                   10                  15

Glu Val Gln Tyr Gly Lys Phe Glu Ala Arg Met Lys Met Ala Ala Ala
                20                  25                  30

Ser Gly Thr Val Ser Ser Met Phe Leu Tyr Gln Asn Gly Ser Glu Ile
                35                  40                  45

Ala Asp Gly Arg Pro Trp Val Glu Val Asp Ile Glu Val Leu Gly Lys
 50                  55                  60

Asn Pro Gly Ser Phe Gln Ser Asn Ile Ile Thr Gly Lys Ala Gly Ala
 65                  70                  75                  80

Gln Lys Thr Ser Glu Lys His His Ala Val Ser Pro Ala Ala Asp Gln
                85                  90                  95

Ala Phe His Thr Tyr Gly Leu Glu Trp Thr Pro Asn Tyr Val Arg Trp
                100                 105                 110
```

```
Thr Val Asp Gly Gln Glu Val Arg Lys Thr Glu Gly Gly Gln Val Ser
            115                 120                 125

Asn Leu Thr Gly Thr Gln Gly Leu Arg Phe Asn Leu Trp Ser Ser Glu
        130                 135                 140

Ser Ala Ala Trp Val Gly Gln Phe Asp Glu Ser Lys Leu Pro Leu Phe
145                 150                 155                 160

Gln Phe Ile Asn Trp Val Lys Val Tyr Lys Tyr Thr Pro Gly Gln Gly
                165                 170                 175

Glu Gly Gly Ser Asp Phe Thr Leu Asp Trp Thr Asp Asn Phe Asp Thr
            180                 185                 190

Phe Asp Gly Ser Arg Trp Gly Lys Gly Asp Trp Thr Phe Asp Gly Asn
        195                 200                 205

Arg Val Asp Leu Thr Asp Lys Asn Ile Tyr Ser Arg Asp Gly Met Leu
    210                 215                 220

Ile Leu Ala Leu Thr Arg Lys Gly Gln Glu Ser Phe Asn Gly Gln Val
225                 230                 235                 240

Pro Arg Asp Asp Glu Pro Ala Pro Asn Ser Ser Val Asp Lys Leu Ala
                245                 250                 255

Ala Ala Leu Glu His His His His His His
            260                 265

<210> SEQ ID NO 15
<211> LENGTH: 266
<212> TYPE: PRT
<213> ORGANISM: Artificial Sequence
<220> FEATURE:
<223> OTHER INFORMATION: Fusion peptide

<400> SEQUENCE: 15

Met Val Ser Ala Lys Asp Phe Ser Gly Ala Glu Leu Tyr Thr Leu Glu
1               5                   10                  15

Glu Val Gln Tyr Gly Lys Phe Glu Ala Arg Met Lys Met Ala Ala Ala
            20                  25                  30

Ser Gly Thr Val Ser Ser Met Phe Leu Tyr Gln Asn Gly Ser Glu Ile
        35                  40                  45

Ala Asp Gly Arg Pro Trp Val Glu Val Asp Ile Glu Val Leu Gly Lys
    50                  55                  60

Asn Pro Gly Ser Phe Gln Ser Asn Ile Ile Thr Gly Lys Ala Gly Ala
65                  70                  75                  80

Gln Lys Thr Ser Glu Lys His His Ala Val Ser Pro Ala Ala Asp Gln
                85                  90                  95

Ala Phe His Thr Tyr Gly Leu Glu Trp Thr Pro Asn Tyr Val Arg Trp
            100                 105                 110

Thr Val Asp Gly Gln Glu Val Arg Lys Thr Glu Gly Gly Gln Val Ser
            115                 120                 125

Asn Leu Thr Gly Thr Gln Gly Leu Arg Phe Asn Leu Trp Ser Ser Glu
        130                 135                 140

Ser Ala Ala Trp Val Gly Gln Phe Asp Glu Ser Lys Leu Pro Leu Phe
145                 150                 155                 160

Gln Phe Ile Asn Trp Val Lys Val Tyr Lys Tyr Thr Pro Gly Gln Gly
                165                 170                 175

Glu Gly Gly Ser Asp Phe Thr Leu Asp Trp Thr Asp Asn Phe Asp Thr
            180                 185                 190

Phe Asp Gly Ser Arg Trp Gly Lys Gly Asp Phe Thr Phe Asp Gly Asn
        195                 200                 205
```

-continued

Arg Val Asp Leu Thr Asp Lys Asn Ile Tyr Ser Arg Asp Gly Met Leu
    210                 215                 220

Ile Leu Ala Leu Thr Arg Lys Gly Gln Glu Ser Phe Asn Gly Gln Val
225                 230                 235                 240

Pro Arg Asp Asp Glu Pro Ala Pro Asn Ser Ser Val Asp Lys Leu Ala
                245                 250                 255

Ala Ala Leu Glu His His His His His His
            260                 265

<210> SEQ ID NO 16
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 16

Asn Ser Ser Val Asp Lys Leu Ala Ala Ala Leu Glu His His His His
 1               5                  10                  15

His His

<210> SEQ ID NO 17
<211> LENGTH: 27
<212> TYPE: DNA
<213> ORGANISM: Artificial Sequence
<220> FEATURE:
<223> OTHER INFORMATION: Primer

<400> SEQUENCE: 17
cagccggcga tggccatggt tagcgca                                          27

<210> SEQ ID NO 18
<211> LENGTH: 29
<212> TYPE: DNA
<213> ORGANISM: Artificial Sequence
<220> FEATURE:
<223> OTHER INFORMATION: Primer

<400> SEQUENCE: 18
ctgctagaag aattcggagc aggttcgtc                                        29

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
cctgctccgt aatcgagctc c                                                21

<210> SEQ ID NO 20
<211> LENGTH: 31
<212> TYPE: DNA
<213> ORGANISM: Artificial Sequence
<220> FEATURE:
<223> OTHER INFORMATION: Primer

<400> SEQUENCE: 20
ctggggcaag ggtgacttca catttgacgg t                                     31

<210> SEQ ID NO 21
<211> LENGTH: 30

```
-continued

<212> TYPE: DNA
<213> ORGANISM: Artificial Sequence
<220> FEATURE:
<223> OTHER INFORMATION: Primer

<400> SEQUENCE: 21
tacgctgcag ttagcgcaaa ggattttagc                              30

<210> SEQ ID NO 22
<211> LENGTH: 35
<212> TYPE: DNA
<213> ORGANISM: Artificial Sequence
<220> FEATURE:
<223> OTHER INFORMATION: Primer

<400> SEQUENCE: 22
tagttctaga tcacggagca ggttcgtcat ctctc                        35
```